US006761884B1

(12) United States Patent
Blaese et al.

(10) Patent No.: US 6,761,884 B1
(45) Date of Patent: *Jul. 13, 2004

(54) VECTORS INCLUDING FOREIGN GENES AND NEGATIVE SELECTIVE MARKERS

(75) Inventors: Michael Blaese, Rockville, MD (US); W. French Anderson, Bethesda, MD (US); Jeanne R. McLachlin, Watkinsville, GA (US); Yawen L. Chiang, Potomac, MD (US); Martin Eglitis, Kensington, MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/289,832

(22) Filed: Aug. 12, 1994

Related U.S. Application Data

(63) Continuation of application No. 07/792,281, filed on Nov. 14, 1991, now abandoned.

(51) Int. Cl.$^7$ .......................... A61K 48/00; C12N 5/10
(52) U.S. Cl. .................. 424/93.2; 435/69.1; 435/172.3
(58) Field of Search ........................ 435/240.2, 240.1, 435/320.1, 235.1, 1.1, 455, 69.1, 172.3; 424/93 A, 93 R, 93 B, 93.1, 93.2

(56) References Cited

U.S. PATENT DOCUMENTS

| | | | | | |
|---|---|---|---|---|---|
| 5,399,346 | A | * | 3/1995 | Anderson et al. | 424/93.21 |
| 5,487,992 | A | * | 1/1996 | Capecchi et al. | 435/172.3 |
| 5,925,345 | A | * | 7/1999 | Blaise et al. | 424/93.2 |

FOREIGN PATENT DOCUMENTS

| | | | |
|---|---|---|---|
| EP | 0 415 731 A2 | * | 3/1991 |
| EP | 0415731 A2 | * | 3/1991 |
| WO | WO89/09271 | | 10/1989 |
| WO | WO90/01547 | | 2/1990 |
| WO | WO90/07936 | * | 7/1990 |
| WO | WO9007936 | * | 7/1990 |
| WO | WO9106658 | * | 5/1991 |
| WO | WO 91/06658 | * | 5/1991 |
| WO | WO9110728 | * | 7/1991 |
| WO | WO91/10729 | * | 7/1991 |
| WO | WO92/08796 | | 5/1992 |
| WO | WO93/02556 | | 2/1993 |

OTHER PUBLICATIONS

Moolten et al. Journal of the National Cancer Institute 82:297–300, Feb. 1990.*
Zwiebel et al. Annals of New York Academy of Science 618:394–404, 1990.*
Mahley Science 240:622–630, Apr. 1988.*
Cox et al. New England Journal of Medicine 299:121–1424, 1978.*
H Temin (1990) Human Gene Therapy 1: 111–123.*
DW Cox et al. (1978) New England J Medicine 299: 1421–1424.*
RW Mahley (1988) Science 240: 622–630.*
F.L. Moolten et al (1990) Journal of the National Cancer Institute 82 (4): 297–300.*
B. Gansbacher et al (1991) J. Cellular Biochemistry Suppl 15, Part G, p. 20, Abstract S218.*
J.G. Hellerman et al (1984) Proc. Natl. Acad. Sci. USA 81: 5340–5344.*
R.A. Fleischman (1991) Amer. Jour. of Med. Sci. 301 (5): 353–363.*
J.A. Zwiebel et al (1990) Ann. N.Y. Acad. Sci. 618: 394–404.*
R.A. Fleischman (1991) Amer. Jour. of Med. Sci. 301(5): 353–363.*
J.A. Zwiebel et al. (1990). Ann. N.Y. Acad. Sci. 618: 394–404.*
F.L. Moolten et al. (1990). Jour. of the National Cancer Institute 82(4): 297–300.*
B. Gansbacher et al. (1991). Jour. Cellular Biochemistry Suppl 15, Part G, p. 20, Abstract S218.*
Moolten, *Cancer Research*, vol. 46, pp. 5276–5281 (Oct. 1986).
Plautz, et al., *The New Biologist*, vol. 3, No. 7, pp. 709–715 (Jul. 1991).
Breakfield, *Neurobiology of Aging*, vol. 10, pp. 647–648 (1989).
Selden, et al., *Science*, vol. 236, pp. 714–718 (May 8, 1991).
Borrelli, et al., PNAS, vol. 85, pp. 7572–7576 (Oct. 1988).
Heyman, et al., PNAS, vol. 86, pp. 2698–2702 (Apr. 1989).
Borrelli, et al., *Nature*, vol. 339, pp. 538–541 (Jun. 15, 1989).
Moolten, et al., *Human Gene Therapy*, vol. pp. 125–134 (1990).

* cited by examiner

Primary Examiner—Deborah Crouch
Assistant Examiner—Joseph Woitach
(74) Attorney, Agent, or Firm—Elliot M. Olstein; Raymond J. Lillie (57) ABSTRACT

A vector, in particular a retroviral vector, which includes a heterologous or foreign gene and a gene encoding a negative selective marker. The negative selective marker enables one to kill cells which contain the gene encoding the negative selective marker, when a particular agent is administered to such cells.

26 Claims, 6 Drawing Sheets

SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGAC | GGATCC | CTCGAG | AAGCTT | GGGCCC |
| G | CGCCGGCG | ATGCAT | CAGCTG | CCTAGG | GAGCTC | TTCGAA | CCCGGG |

1/2ClaI
AT
TAGC

FIG. 2

THE SEQUENCE OF THE MULTIPLE CLONING SITE OF THE pGENE SHUTTLE SYSTEM

| SphI | NotI | SnaBI | SalI | SacII | ACCI | NruI | BglII |
|---|---|---|---|---|---|---|---|
| GGCATG | GCGGCCGC | TACGTA | GTCGAC | CCGCGG | GTCGAC | TCGCGA | AGATCT |
| CCGTAC | CGCCGGCG | ATGCAT | CAGCTG | GGCGCC | CAGCTG | AGCGCT | TCTAGA |

LEADER TRANSLATION
SEQUENCE INITIATION     NcoI                          XhoI    HindIII
TTCCGCAGCAGCCGCCA       CCATGG...INSERTED GENE ...    CTCCAG  AAGCTT
AAGGCGTCGTCGGCGGT       GGTACC                        GAGCTC  TTCGAA
                        SmaI
ApaI
GGGCCCGGG
CCCGGGCCC

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 51 bases
      (B) TYPE: nucleic acid
      (C) STRANDEDNESS: single
      (D) TOPOLOGY: linear    (ii) MOLECULE TYPE: plasmid DNA    (xi) SEQUENCE DESCRIPTION: SEQ ID NO: 1:

AATTCGCGGC CGCTACGTAG TCGACGGATC CCTCCAGAAG CTTGGGCCCA T      51

(2) INFORMATION FOR SEQ ID NO:2:

(i) SEQUENCE CHARACTERISTICS:
      (A) LENGTH: 94 base pairs
      (B) TYPE: nucleic acid
      (C) STRANDEDNESS: single
      (D) TOPOLOGY: linear -continued

```
    (ii) MOLECULE TYPE:  plasmid DNA (ix) FEATURE:
         (D) OTHER INFORMATION:  Gene may be inserted between base 73
             and base 74.

(xi) SEQUENCE DESCRIPTION:  SEQ ID NO:2:

CGCATGGCGG CCGCTACGTA GTCGACCCGC GGGTCGACTC GCGAAGATCT TTCCGCAGCA         60

GCCGCCACCA TGGCTCGAGA AGCTTGGGCC CGGG                                    94
```

VECTORS INCLUDING FOREIGN GENES AND NEGATIVE SELECTIVE MARKERS

This application is a continuation of application Ser. No 07/792,281, filed Nov. 14, 1991, abandoned.

This invention relates to vectors, in particular viral vectors such as retroviral vectors, which include heterologous, or foreign genes. More particularly, this invention relates to vectors including heterologous gene(s) and a negative selective marker.

Vectors are useful agents for introducing heterologous, or foreign, gene(s) or DNA into a cell, such as a eukaryotic cell. The heterologous, or foreign gene(s) is controlled by an appropriate promoter. In addition, the vector may further include a selectable marker, such as, for example, a neomycin resistance ($neo^R$) gene, a hygromycin resistance ($hygro^R$) gene, or a β-galactosidase (β-gal) gene, said marker also being under the control of an appropriate promoter. Examples of such vectors include prokaryotic vectors, such as bacterial vectors; eukaryotic vectors, including fungal vectors such as yeast vectors; and viral vectors such as DNA virus vectors, RNA virus vectors, and retroviral vectors. Retroviral vectors which have been employed for introducing heterologous, or foreign, genes or DNA into a cell include Moloney Murine Leukemia Virus, spleen necrosis virus, and vectors derived from retroviruses such as Rous Sarcoma Virus and Harvey Sarcoma Virus. The term "introducing" as used herein encompasses a variety of methods of introducing heterologous, or foreign, genes or DNA into a cell, such methods including transformation, transduction, transfection, and infection.

In accordance with an aspect of the present invention, there is provided a vector which includes a heterologous, or foreign gene, and a gene encoding a negative selective marker.

The vector which includes the heterologous, or foreign, gene, and the gene encoding a negative selective marker, may be a prokaryotic vector, such as a bacterial vector; a eukaryotic vector, such as a fungal vector, examples of which include yeast vectors; or a viral vector such as a DNA viral vector, an RNA viral vector, or a retroviral vector.

In a preferred embodiment, the vector is a viral vector, and in particular a retroviral vector. Examples of retroviral vectors which may be produced to include the heterologous gene and the gene encoding the negative selective marker include, but are not limited to, Moloney Murine Leukemia Virus, spleen necrosis virus, and vectors derived from retroviruses such as Rous Sarcoma Virus, Harvey Sarcoma Virus, Avian leukosis virus, human immunodeficiency virus, myeloproliferative sarcoma virus, and mammary tumour virus.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

Bender et al., J. Virol. 61:1639–1649 (1987) have described a series of vectors, based on the N2 vector (Armentano, et al., J. Virol., 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point. In Moloney murine leukemia virus (MoMuLV), 5' to the authentic gag start, an open reading frame exists which permits expression of another glycosylated protein ($pPr80^{gag}$). Moloney murine sarcoma virus (MoMuSV) has alterations in this 5' region, including a frameshift and loss of glycosylation sites, which obviate potential expression of the amino terminus of $pPr80^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller et al., Biotechniques, 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral vector may include at least four cloning, or restriction enzyme recognition sites, wherein at least two of the 'sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vectors of the present invention include one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

Heterologous or foreign genes which may be placed into the vectors of the present invention include, but are not limited to genes which encode cytokines or cellular growth factors, such as lymphokines, which are growth factors for lymphocytes. Other examples of foreign genes include, but are not limited to, genes encoding soluble CD4, Factor VIII, Factor IX, ADA, the LDL receptor, ApoE, and ApoC.

Suitable promoters which may control the foreign genes include those hereinabove described.

The vector also includes a gene encoding a suitable negative selective marker. An example of a negative selective marker is a gene which encodes thymidine kinase, or TK marker. It is to be understood, however, that the scope of the present invention is not to be limited to any specific negative selective marker or markers.

The vector of the present invention may be used to transduce packaging cells and to generate infectious viral particles. The infectious viral particles may be used to transduce cells (eg., eukaryotic cells such as mammalian cells). The vector containing the heterologous gene and the gene encoding the negative selective marker may transduce the packaging cells through any means known in the art. Such means include, but are not limited to, electroportation, the use of liposomes, and CaPO$_4$ precipitation. The eukaryotic cells may then be administered in vivo to a host as part of a gene therapy procedure. The eukaryotic cells which contain the infectious viral particles, as well as any other cells which are generated that contain the foreign gene and the gene encoding the negative selective marker, may be killed through the in vivo administration of an agent to a host. The selection of a suitable agent is dependent upon the heterologous gene and the gene encoding the negative selective marker contained in the vector.

For example, when the heterologous gene encodes a lymphokine, the negative selective marker may be a gene which encodes for thymidine kinase, or TK. When, for example, such a vector, which includes a heterologous gene encoding for a lymphokine, and a gene encoding for thymidine kinase as a negative selective marker, is employed to generate infectious viral particles, such infectious viral particles may be used to transfect tumor induced lymphocytes, or TIL cells. Such cells may then be administered to a host. The lymphokine may stimulate the production of tumor cells in the host. To prevent the further generation of cells containing the gene encoding the lymphokine and thus preventing the production of tumor cells, one may administer ganciclovir to the host. The ganciclovir may be administered in vivo and preferably by intravenous injection. In the presence of ganciclovir, such transfected tumor induced lymphocytes, and all other cells containing the gene encoding the lymphokine and the gene encoding thymidine kinase, are killed.

The vectors of the present invention may be produced from existing vectors through genetic engineering techniques known in the art such that the resulting vector includes a heterologous or foreign gene and a gene encoding a negative selective marker.

In accordance with an alternative aspect of the present invention, there is provided a vector system for the transduction of cells (e.g., eukaryotic cells and in particular mammalian cells) which comprises a first vector which includes a foreign gene, and a second vector which includes a gene encoding a negative selective marker. Each of the first and second vectors may be of the types hereinabove described, and may be constructed through genetic engineering techniques known to those skilled in the art. The foreign gene contained in the first vector may encode for those substances hereinabove described. The gene encoding the negative selective marker may be a gene encoding for thymidine kinase as hereinabove described, or any other negative selective marker. The first and second vectors may be used to tranduce packaging cells through techniques known in the art, and to generate infectious viral particles. The infectious viral particles generated from the first and second vectors may then be used to tranduce cells, such as eukaryotic, and in particular, mammalian cells, which then may be administered to a host as part of a gene therapy procedure.

BRIEF DESCRIPTION OF THE DRAWINGS

The invention now will be described with respect to the drawings, wherein.

The invention will now be described with respect to the following example; however, the scope of the present invention is not intended to be limited thereby.

EXAMPLE

Construction of TK/IL-2 (Interleukin-2) Vector

The following describes the construction of the G1I21SvTk vector, which includes a gene for interleukin 2 (IL-2) and a gene for thymidine kinase (TK).

Figure 1:
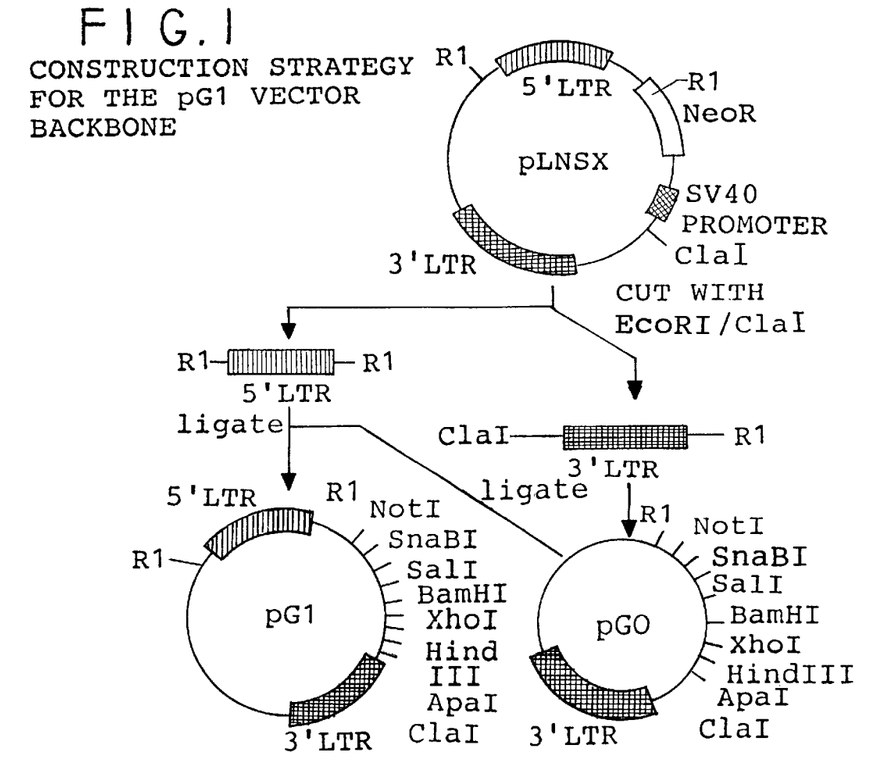
FIG. 1 is a schematic of the construction of the pG1 vector backbone.
Figure 2:
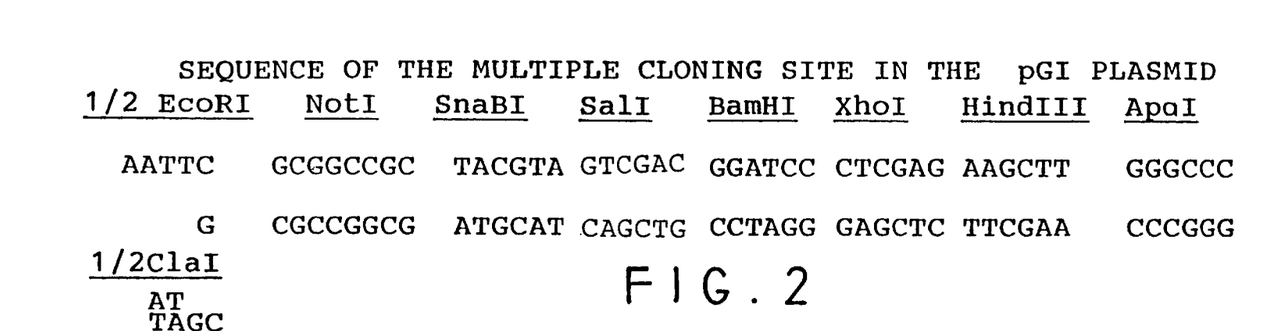
FIG. 2 shows the sequence of the multiple cloning site of the pG1 plasmid.

The GlI21SvTk vector is derived from plasmid pG1. The plasmid pG1 was constructed from pLNSX (Palmer et al., *Blood*, 73:438–445; 1989). The construction strategy for plasmid pG1 is shown in FIG. 1. The 1.6 kb EcoRI fragment, containing the 5' Moloney Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pGO. The plasmid pGO was used to generate the vector plasmid pG1 by the insertion of the 1.6 kb EcoRI fragment containing the 5' LTR into the unique EcoRI site of pGO. Thus, pG1 consists of a retroviral vector backbone composed of a 5' portion derived from MoMuSV, a short portion of gag in which the authentic ATG start codon has been mutated to TAG (Bender et al. 1987), a 54 base pair multiple cloning site (MCS) containing, from 5' to 3' the sites EcoRI, NotI, SnaBI, SalI, BamHI, XhoI, HindII, ApaI, and ClaI, and a 3' portion of MoMuLV from base pairs 7764 to 7813 (numbered as described (Van Beveren et al., Cold Spring Harbor, Vol. 2, pg. 567, 1985) (FIG. 2). The MCS was designed to generate a maximum number of unique insertion sites, based on a screen of non-cutting restriction enzymes of the pG1 plasmid, the neo$^r$ gene, the β-galactosidase gene, the hygromycin$^r$ gene, and the SV40 promoter.

Figure 3:
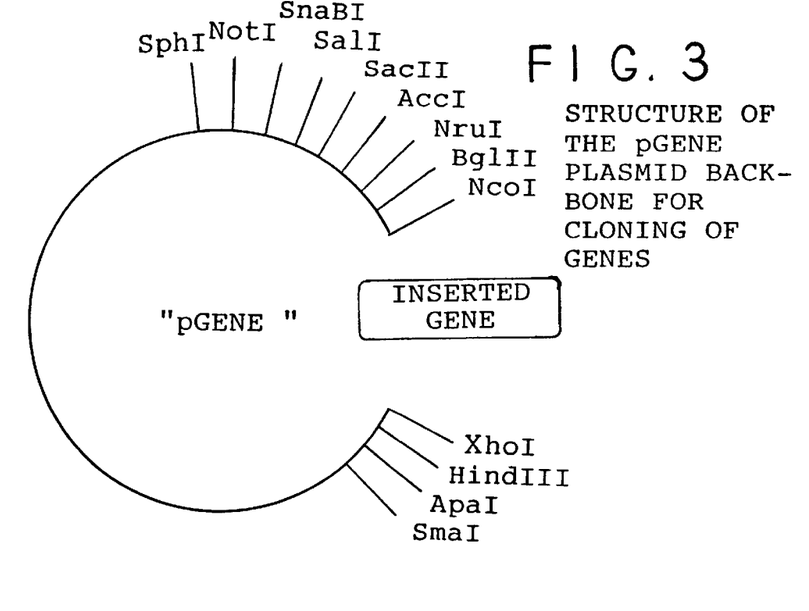
FIG. 3 is a schematic of the pGene plasmid backbone.
Figure 4:
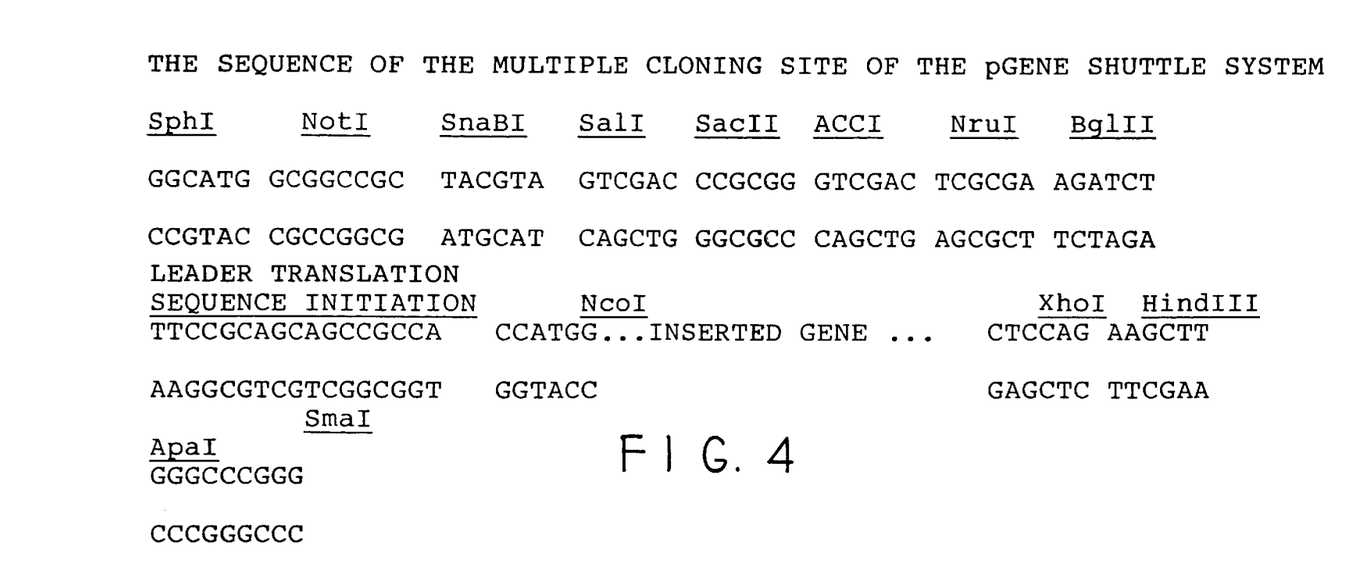
FIG. 4 shows the sequence of the multiple cloning site for the pGene shuttle plasmid.
Figure 5:
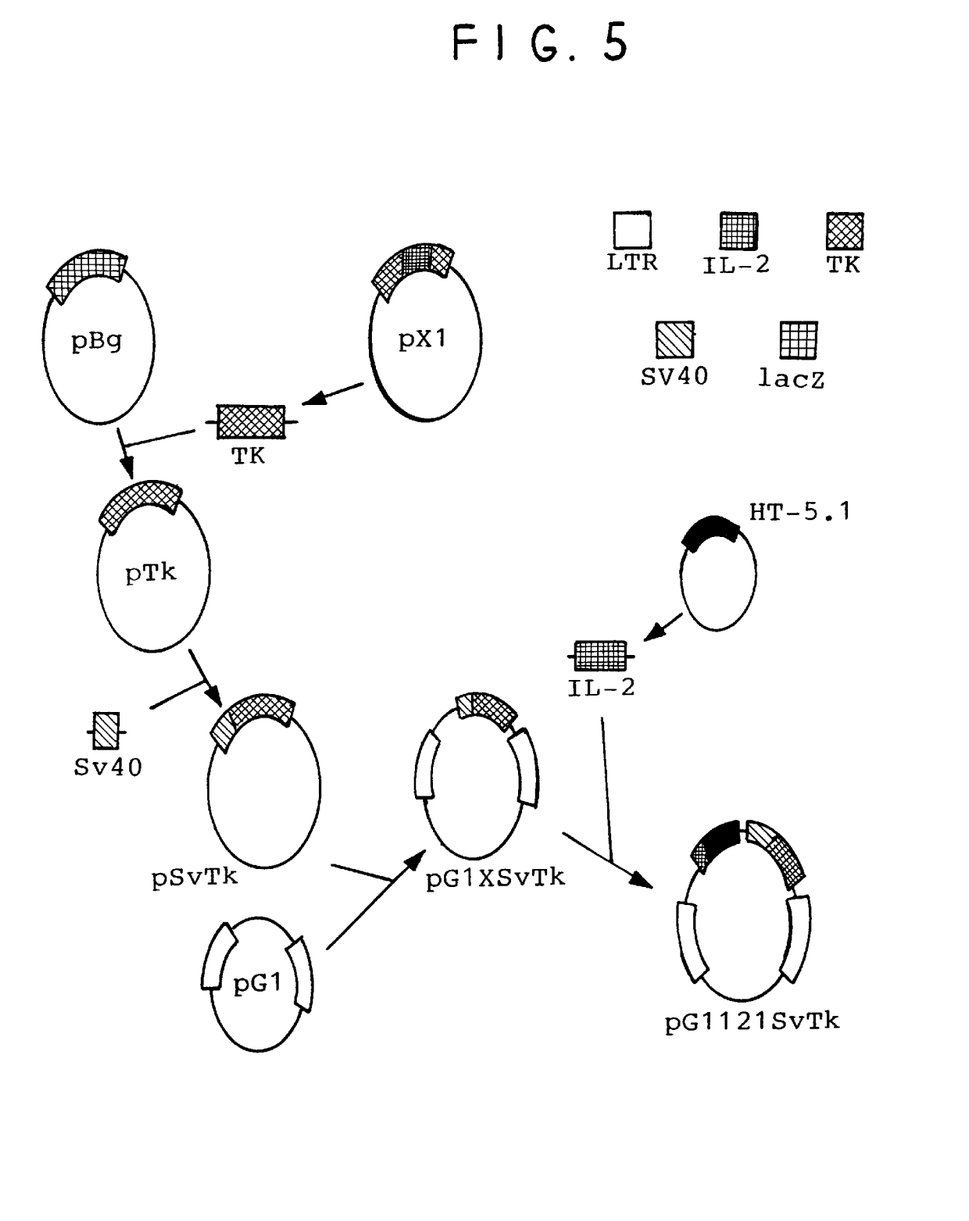
FIG. 5 is a schematic of the construction of the plasmid pG1I21SvTK.

The pGene plasmid (FIG. 3) does not exist as an independent molecular entity, but rather may be considered a construction intermediate in the process of cloning genes for subsequent insertion into pG1. The basic backbone is that of pBR322 (Bolivar et al., *Gene*, 2:95 (1977)). To the 2.1 kb EcoRI/NdeI fragment containing the ampicillin resistance gene and the bacterial origin of replication two linkers were ligated. These linkers, synthesized using an oligo-nucleotide synthesizer, contain a total of 14 unique restriction enzyme recognition sites, as well as sequences felt to enhance mRNA stability and translatability in eukaryotic cells. The restriction sites were chosen based on a screen of non-cutting restriction enzymes of the plasmid backbone, the neo$^r$ gene, the β-galactosidase gene, the hygromycin$^r$ gene, and the SV40 promoter. (The choice of enzymes results in the sites of pG1 being a subset of the sites in pGene). Genes can be ligated into this backbone with NcoI and XhoI ends. The resulting backbone, less the inserted gene, is roughly 2.1 kb in size and contains a 99 base pair multiple cloning site containing, from 5' to 3', the following restriction enzyme recognition sites: SphI, NotI, SnaBI, SalI, SacII, AccI, NruI, BglI, NcoI, XhoI, HindIII, ApaI, and SmaI. (FIG. 4). From the BglI to the NcoI sites lies a 27 base pair region containing an mRNA signal based on the work of Hagenbuchle et al. *Cell*, 13:551–563 (1978). They found that the 3' terminal sequence of 18S ribosomal RNA is highly conserved among eukaryotes, suggesting that complementary sequences between 18S RNA and mRNA may be involved in positioning the initiating start codon (AUG) on the 30S ribosome. Synthesis of adenovirus 2 late proteins, particularly polypeptide IX, may also follow this rule (Lawrence and Jackson, *J. Molec. Biology*, 162:317–334) (1982)). Following this ribosomal binding signal, a consensus signal for initiation of translation based on Kozak's rules (Kozak, Nucl. Acids Res., 12:857–872, 1984) was also inserted. We used the wobble at the ATG which permitted use of an NcoI restriction enzyme site.

To make pG1I21SvTk, the plasmid pG1XSvTK was first constructed. First, the Herpes thymidine kinase (TK) gene was subcloned into pBg.

To make pBg, the 3.0 kb BamHI/EcoRI fragment of the lacZ gene encoding β-galactosidase was isolated and two linkers were added. To the 5' end an NdeI-BamHI linker, containing the 5' portion of the multiple cloning site up to the NcoI site, as well as the first 21 base pairs of the lacZ gene, was ligated. To the 3' end, an EcoRI/EcoRI linker completing the 3' sequence of the lacZ followed by sequence encoding the XhoI, HindIII, ApaI, and SmaI sites was ligated. The sequence of the 5' EcoRI site was mutated, maintaining amino acid coding fidelity but eliminating the internal EcoRI site to permit directional cloning and screening of the total linkered lacZ fragment into the 2.1 kb NdeI/EcoRI of pBR322. The pBg plasmid was then used to construct an SV40 promoted TK gene. A 1.74 kb Bgl II/PvuII fragment containing the Herpes Virus Type I thymidine kinase gene, was excised from the pX1 plasmid (*Huberman et al., Expt*1. *Cell Res.*, Vol 153, pgs. 347–362 (1984)), blunted with the large (Klenow) fragment of DNA polymerase I, and inserted into pBg which had first digested with NcoI and XhoI and then also blunted. This resulted in plasmid pTk. The 339 base pair PvuII/HindIII SV40 early promoter fragment was then inserted into pTk which had been digested with SalI and BglII to generate the plasmid pSvTk. Once pSvTk was obtained, it was a simple matter to obtain the SalI/XhoI fragment containing the SV40-promoted TK gene, blunt it with the large Klenow fragment of DNA polymerase I, and insert it into SalI/HindIII digested and blunted pG1, thereby generating pG1XSvTk.

The plasmid pG1I21SvTk was prepared as follows. The IL-2 gene was derived from the plasmid HT-5.1 (ATCC #59396). The 1.0 kb BamHI fragment was isolated from this plasmid and then truncated down to a 445 base pair HgiAI/DraI fragment. To restore the authentic 5' coding sequence, a 100 base pair linker was constructed including the entire 20 amino acid coding region of the amino-terminal end of IL-2, and then a 40 base pair stretch identical in sequence to that of pGene between the BglII and NcoI sites is added as a 5' leader. A SnaBI site was added 5' to the BglII, permitting direct insertion of this reconstructed IL-2 fragment into pBg which has been digested with SnaBI and HindIII (the HindIII blunted with the Klenow polymerase). From this resulting pI21 plasmid, a 550 base pair BglII/ClaI fragment was isolated blunted, and then inserted into Not I digested and blunted pG1XSvTk.

Generation of Producer Cells

Producer cells for vectors carrying the Herpes simplex virus thymidine kinase gene (TK) as a marker may be generated in two ways. Both methods are developed to generate producer cells containing only a single, provirally integrated vector within the chromosomes of the packaging cell. In the first, the TK gene is co-transfected into PE501 packaging cells (Miller and Rosman, *Biotechniques*

7:980–990 (1989) with an alternate selectable plasmid, such as pSv2Neo. Once a population of transfected cells is selected based on the neo$^r$ selectable marker gene of the pSv2Neo plasmid, the PE501 cells are mixed with PA317 amphotropic packaging cells made hygromycin resistant (hygro$^r$) with a hygromycin phosphotransferase expressing plasmid, and allowed to culture together for 10–14 days. At the end of this culture period, the PA317 cells, infected with the TK vector packaged in the PE501 cells, are recovered by hygromycin selection. Individual hygro$^r$ clones are isolated and evaluated for expression of the non-selectable gene (in the above example IL-2), as well as for their ability to transduce target cells. The latter is measured either by the level of non-selectable gene activity that is introduced in target cells, or by direct TK titering using HAT selection (Littlefield, Science 145:709–710 (1964)) of TK- NIH 3T3 fibroblasts in a manner similar to conventional titering with G418 for the neo$^r$ gene (Eglitis et al, Science 230:1395–1398 (1985)). Briefly, TK- NIH 3T3 cells are plated at a density of 2×10$^4$ cells per 35 mm dish and the following day infected for 2–4 hours with various dilutions of virus supernatant containing 8 µg/ml polybrene. The cells are allowed to grow for an additional 24–48 hours following infection and then were grown in selective medium containing HAT for 10–12 days prior to staining with methylene blue and counting individual HAT resistant colonies. Producer clones which generate between 5×10$^4$ and 5×10$^5$ HAT resistant colony-forming units per ml are then used for further evaluation of efficacy.

A second method utilizes amphotropic packaging cells which are TK-. Having packaging cells which are TK- is important to generate easily trans-infected producer clones of vectors which only contain the TK gene as selectable marker. It is desired to incorporate packaging functions into cells lacking endogenous TK activity so that when TK vector is introduced the resulting vector-containing cells may be directly selected in HAT medium. A means of accomplishing this is to use the pPAM3 packaging system of Miller et al., *Mol. Cell. Biol.*, 5:431–437 (1985). The pPAM3 plasmid, encoding for gag, pol, and env, is transfected into TK- NIH 3T3 cells (Chen and Okayama, *Mol. Cell. Biol.*, 7:2745–2752 (1987) along with a plasmid containing a co-selectable marker such as Sv2Neo (Southern and Berg, *J. Molec. Appl. Genet*, 1:327–341 (1982)). Cells maximally expressing the env gene are the isolated using antibody specific to env in conjunction with flow cytometry. One can then use this population of high env expressing pPAM3 transfected TK- cells (PAT cells) as the target for trans-infection with vector transiently expressed from an ectotropic packaging cell line 48 hours after high effeciency calcium phosphate transfection. The vector transiently packaged by ectropic packaging cells is used to infect directly the amphotropic PAT cells. Transinfected clones are selected with HAT, and then evaluated as described above.

Example 2

Figure 6:
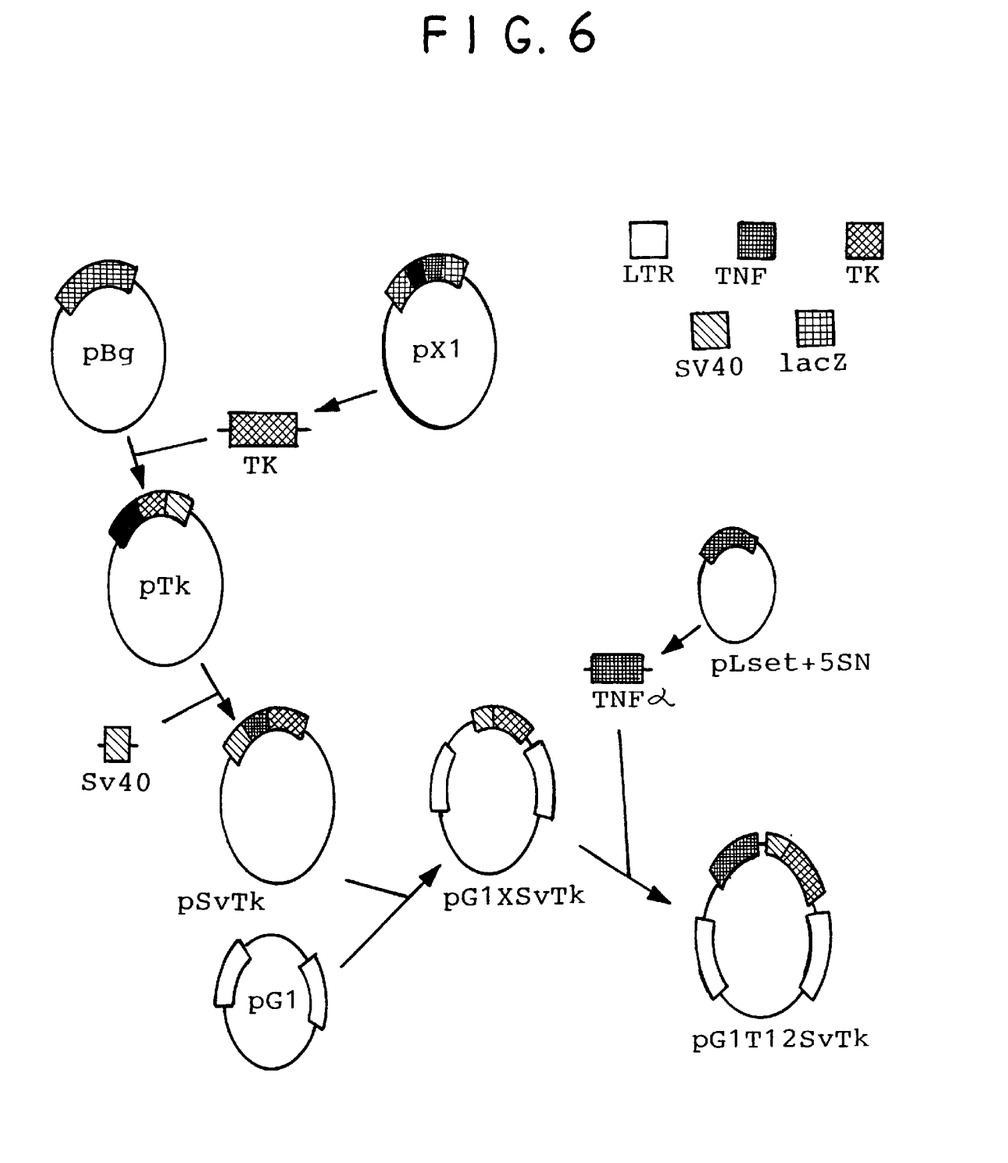
FIG. 6 is a schematic of the construction of the plasmid pG1T12SvTK.

This example describes the construction of pG1T12SvTK, which contains a gene encoding TNF-α. A schematic of the construction of pG1T12SvTK is shown in FIG. 6.

Plasmid pG1XSvTK was constructed as hereinabove described in Example 1. Then, the plasmid pLset5SN was constructed. Plasmid pLset5SN contains a 521 bp NcoI/EcoRI fragment from pTNF-A.BEC (Beckman Catalogue number 267430, and as published in Pennica, et al., *Nature*, Vol. 312, pg. 724 (1984)) to which had been fused a 51 bp EcoRI/NruI oligomer encoding the natural secretion signal of TNF-α.

To create the full and authentic sequence of TNF-α, a set of 10 oligonucleotides was synthesized and assembled in sets of two or four. The sequence of these oligonucleotides was formulated using the human TNF-α sequence found in Genbank (Accession number X02159). For convenience of cloning, the oligomers were assembled and ligated to the 5' end of the 521 bp TNF-α fragment from pTNF-A.BEC using the pLXSN plasmid (Miller, et al., *Biotechniques*, Vol. 7, pgs. 980–991 (1990)). A series of plasmid intermediates, pLSET1SN and pLSET3SN AND LSET4SN, each containing greater assemblages of oligonucleotide fragments, were constructed. To construct pLSET5SN, an 851 bp HindIII fragment from pLSET4SN containing the majority of the TNF-α coding sequence was cloned into the unique HindIII site of pLSET3SN immediately following the assembled sequence for the secretion signal. This ligation resulted in the formation of plasmid pLSET5SN, which contains the entire authentic cDNA sequence of TNF-α, including the sequence of the secretion signal. The entire TNF-α gene containing the natural secretion signal was then removed from pLset5SN as a 730 bp BglII/Bam HI fragment. This fragment was then blunted using the Klenow fragment, and inserted into the unique SnaBI site of pG1XSvTk, to create the final construct pG1T12SvTk.

Example 3

Figure 7:
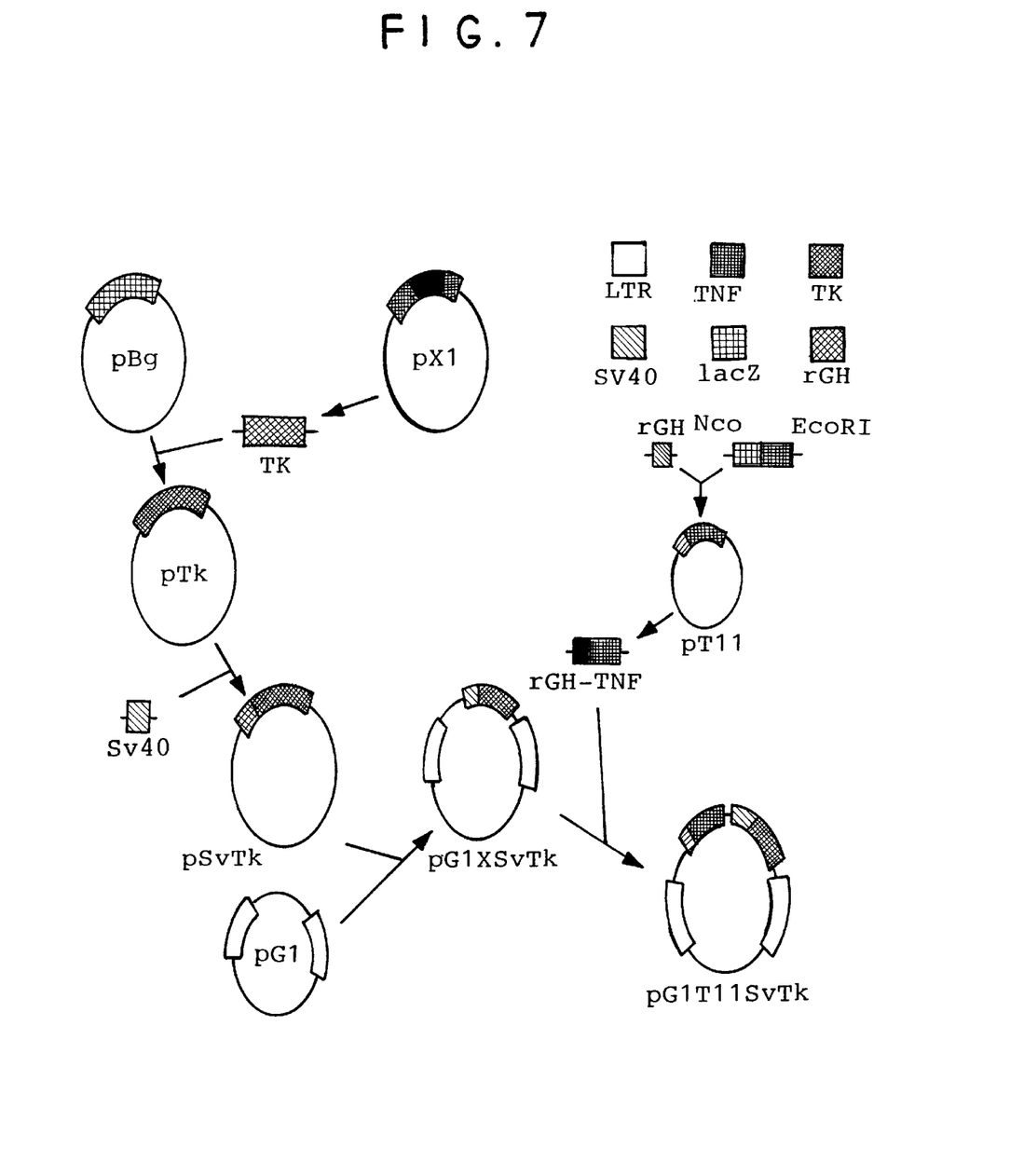
FIG. 7 is a schematic of the construction of the plasmid pG1T11SvTK.

This example describes the construction of pG1T11SvTk, which, like pG1T12SvTk, contains a gene encoding TNF-α. A schematic of the construction of pG1T11SvTk is shown in FIG. 7.

Plasmid pG1XSvTk was constructed as described in Example 1. Then the plasmid pT11 was constructed. The same 521 bp NcoI/EcoRI fragment from pTNF-A.BEC is inserted in place of the lacZ gene in NcoI/EcoRI digested pBG, and an 87 base pair oligomer containing the rat growth hormone secretion signal, as formulated using the rat growth hormone sequence found in Genbank (Accession number J00739; Barta, et al., *Proc. Natl. Acad. Sci. U.S.A.*, Vol. 78, pgs. 4867–4871 (1981)) is then inserted into the NcoI site. The resulting gene is removed as a 608 bp BglII/BamHI fragment, blunted with the Klenow fragment, and inserted into the unique SnaBI site of pG1XSvTk to create pG1T11SvTk.

Example 4

Figure 8:
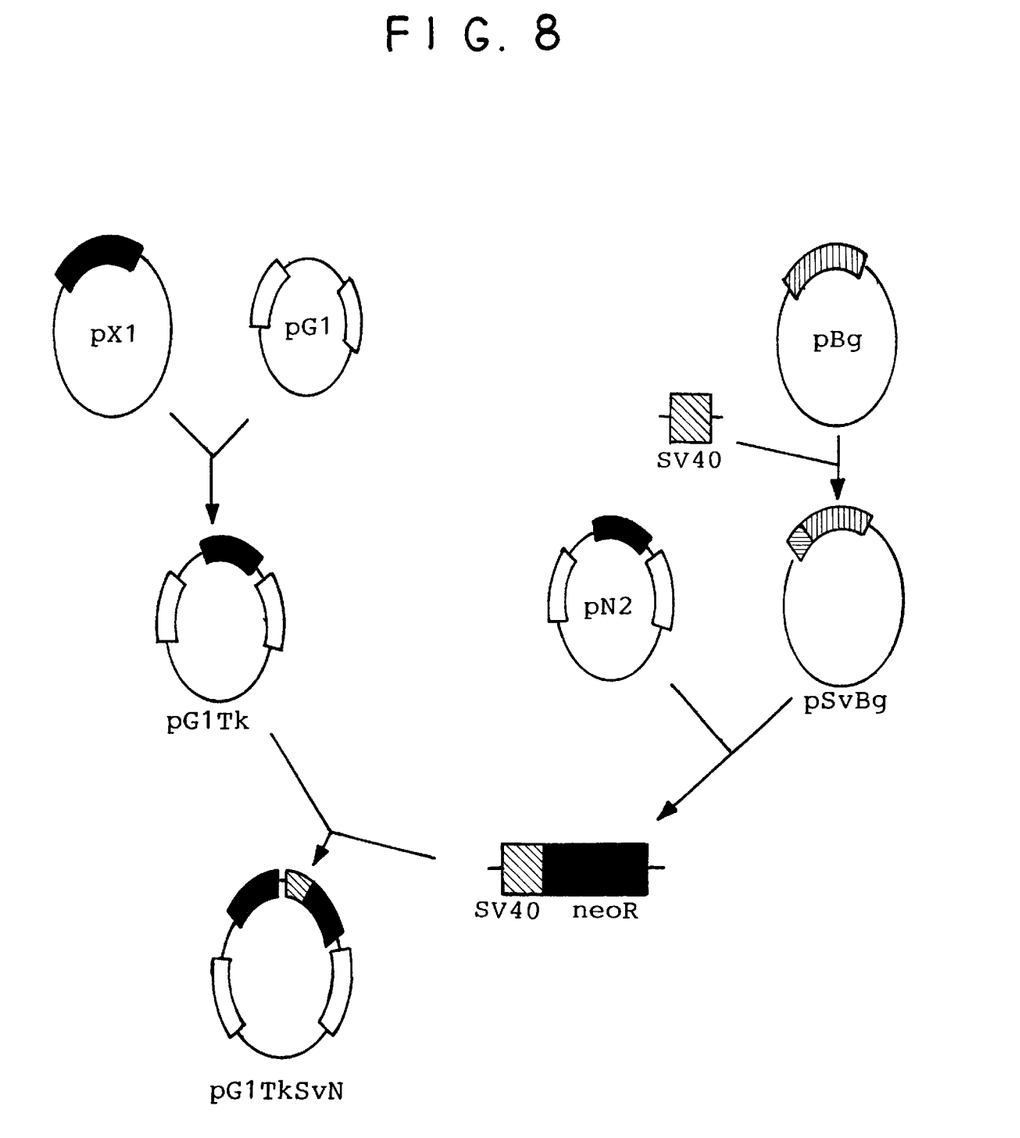
FIG. 8 is a schematic of the construction of the plasmid pG1TKSvN.

This example describes the construction of pG1TkSvN, a schematic of which is shown in FIG. 8. This vector contains a gene, under the control of an SV40 promoter, which encodes neomycin resistance.

Plasmids pG1 and pBg were constructed as described in Example 1. A 1.74 kb BglII/PvuII fragment was excised from the pX1 plasmid, blunted with the large (Klenow) fragment of DNA polymerase I, and inserted into the unique SnaBI site in the pG1 multiple cloning site, to form plasmid pG1TK.

A 339 bp PvuII/HindIII SV40 early promoter fragment was then inserted into pBg in the unique NruI site to generate the plasmid pSvBg. The pSvBg plasmid was digested with BglII/XhoI to remove the lacZ gene, and the ends were made blunt using the Klenow fragment. An 852 bp EcoRI/AsuII fragment containing the coding sequence of the neomycin resistance gene was removed from pN2 (Armentano, et al., *J. Virol.*, Vol. 61, pgs. 1647–1650 (1987)), blunted with Klenow fragment and ligated into the 2.5 kb blunted BglII/XhoI fragment generated hereinabove, resulting in pSvN. The SV40 promoter/neomycin resistance gene cassette was then removed from pSvN as a 1191 bp SalI/HindIII fragment. The pG1Tk plasmid was then digested with SalI/HindIII and ligated with the SV40/neo$^R$ fragment to generate pG1TkSvN. (FIG. 8).

Example 5

This example employs a clone (WP4) (Asher et al., *J. Inmunol*, Vol. 146, pg. 3227 (1991)) of a murine tumor cell line MCA205 (Wexler et al., *J. Natl. Canc. Inst.*, Vol. 63, pg. 1393 (1979)) for assessing the utility of the HSV-TK gene in a "suicide" system.

WP4 cells are plated in 100 mm tissue culture plates at $1-5 \times 10^5$ cells per plate. After 24 hrs. of culture, growth medium is removed and 10 ml of retroviral supernatant containing pG1TKSvN ($10^4-10^5$ titer) with 8 ug/ml polybrene is added per plate. The cells are incubated from 18 to 24 hrs., and the supernatant is then removed and the cells are placed in growth medium for an additional 48 hours of culture. At the end of this period, the cells are from 80% to 90% confluent. Each 100 mm plate is split into three 100 mm paltes, and the cells are grown as follows:

Plate 1: Expand cells and freeze with no further treatment.

Plate 2: Cells are maintained without treatment as an "unselected" population.

Plate 3: One day after splitting, the cells are placed in 0.4–0.8 mg/ml G418, and the cells are observed daily. When 60% to 70% of the cells have been killed, the selection medium is removed, the culture is washed in PBS, and growth medium is added. The cells are cultured for another 5 to 7 days. Cultures which are 50% to 60% confluent are prepared, and 0.4–0.8 mg/ml of G418 in growth medium is added. The cells are then monitored for growth. After initial cell death, the cells can be maintained in G418 continuously. These cells represent the "selected" population.

Transduced "selected" cells are then plated in 24-well tissue culture plate at $1-2.5 \times 10^4$ cells per well. After 24 hrs. of culture, ganciclovir is added in concentrations ranging from 0.01–100 uM, the cells are monitored for growth and all wells are stained in methylene blue when the control wells (no ganciclovir added) are confluent (at 5 to 7 days). Complete killing of transduced selected cells is observed at concentrations from 0.1 to 1.0 uM of ganciclovir, while untransduced cells are killed at concentrations of 100 uM or greater.

Example 6

WP4 tumor cells form tumors in C57BL/6 or BNX mice when injected subcutaneously. The number of cells required for tumor formation will vary depending of the strain of mouse used. C57BL/6 mice require $5 \times 10^6 - 1 \times 10^7$ cells for tumor formation in 10–14 days. BNX mice require $1-5 \times 10^4$ cells for tumor formation in 10–14 days. Tumor cells are suspended in PBS and injected subcutaneously into the hind flank in a 0.5 ml volume. Five to ten days after tumor inoculation, ganciclovir is administered intraperitoneally twice daily for 5 days. A 2–5 mg/ml solution of ganciclovir prepared in serum-free medium (RPMI 1640, DMEM, or other) is used to achieve a dose of 125–150 mg/kg. Animals are monitored and tumor measurements made twice weekly.

At the time of ganciclovir administration, tumors are palpable, but unmeasurable. Tumors arising from untransduced WP4 cells reach a size of 2.0–2.5 cm$^3$ in 40–45 days with or without ganciclovir administration. Tumor cells containing the HSV-TK gene initially form palpable tumors then regress completely and become undetectable within 10–20 days after the start of ganciclovir treatment. Complete, long term tumor ablation is observed in 60–80% of mice having received selected cells plus ganciclovir therapy.

It is to be understood, however, that the scope of the present invention is not to be limited to the specific embodiments described above. The invention may be practiced other than as particularly described and still be within the scope of the accompanying claims.

---

What is claimed is:

1. A method for terminating expression of a heterologous gene in a mammalian cell of a mammalian host, comprising administering to said mammalian host an agent which kills said mammalian cell by interacting with the gene product of a negative selective marker expressed by said mammalian cell, wherein said mammalian cell comprises a vector sequence comprising said heterologous gene and a gene encoding said negative selective marker.

2. The method according to claim 1, wherein said host is a human.

3. The method according to claim 2, wherein said vector sequence comprises a viral vector sequence.

4. The method according to claim 3, wherein said vector sequence comprises a DNA viral vector sequence.

5. The method according to claim 3, wherein said vector sequence comprises an RNA viral vector sequence.

6. The method according to claim 5, wherein said vector sequence comprises a retroviral vector sequence.

7. The method according to claim 6, wherein said retroviral vector sequence has an incomplete structural gene.

8. The method according to claim 5, wherein said retroviral vector sequence has no intact gag, pol or env gene sequences.

9. The method according to claim 8, wherein said retroviral vector sequence has no gag, pol or env sequences.

10. The method according to claim 2, wherein said heterologous gene encodes a growth factor, a lymphokine, soluble CD4, Factor VIII, Factor IX, ADA, LDL receptor, ApoE, or ApoC.

11. An isolated human cell including an RNA viral vector, said RNA viral vector including a heterologous gene encoding a therapeutic agent and a gene encoding a negative selective marker.

12. The human cell of claim 11 wherein said vector is a retroviral vector.

13. The human cell of claim 12 wherein said retroviral vector has an incomplete structural gene.

14. The human cell of claim 12 wherein said retroviral vector has no intact gag, pol, or env gene sequences.

15. The human cell of claim 14 wherein said retroviral vector has no gag, pol, or env gene sequences.

16. The human cell of claim 11, wherein said therapeutic agent is selected from the group consisting of a growth factor, a lymphokine, soluble CD4, Factor VIII, Factor IX, ADA, LDL receptor, ApoE, and ApoC.

17. The human cell of claim 11 wherein said negative selective market is HSV thymidine kinase.

18. The human cell of claim 16 wherein said therapeutic agent is a growth factor.

19. The human cell of claim 16 wherein said therapeutic agent is a lymphokine.

20. The human cell of claim 16 wherein said therapeutic agent is soluble CD4.

21. The human cell of claim 16 wherein said therapeutic agent is Factor VIII.

22. The human cell of claim 16 wherein said therapeutic agent is Factor IX.

23. The human cell of claim 16 wherein said therapeutic agent is ADA.

24. The human cell of claim 16 wherein said therapeutic agent is the LDL receptor.

25. The human cell of claim 16 wherein said therapeutic agent is ApoE.

26. The human cell of claim 16 wherein said therapeutic agent is ApoC.

* * * * *